United States Patent
Hoff et al.

(10) Patent No.: US 6,899,680 B2
(45) Date of Patent: May 31, 2005

(54) ULTRASOUND MEASUREMENT TECHNIQUES FOR BONE ANALYSIS

(75) Inventors: Lars Hoff, Bekkestua (NO); Kjell Oygarden, Skarer (NO)

(73) Assignee: Odetect as, Lorenskog (NO)

(*) Notice: Subject to any disclaimer, the term of this patent is extended or adjusted under 35 U.S.C. 154(b) by 241 days.

(21) Appl. No.: 10/036,072

(22) Filed: Oct. 19, 2001

(65) Prior Publication Data

US 2002/0161300 A1 Oct. 31, 2002

Related U.S. Application Data

(60) Provisional application No. 60/241,609, filed on Oct. 19, 2000.

(51) Int. Cl.[7] .............................................. A61B 8/00
(52) U.S. Cl. ....................................................... 600/449
(58) Field of Search ................................. 600/437–438, 600/449, 458, 585, 459; 73/597, 599, 602

(56) References Cited

U.S. PATENT DOCUMENTS

| 3,720,098 | A | * | 3/1973 | Dixon | 73/597 |
|---|---|---|---|---|---|
| 4,913,157 | A | * | 4/1990 | Pratt et al. | 600/449 |
| 5,143,069 | A | * | 9/1992 | Kwon et al. | 600/437 |
| 5,197,475 | A | | 3/1993 | Antich et al. | |
| 5,259,384 | A | * | 11/1993 | Kaufman et al. | 600/442 |
| 5,309,898 | A | * | 5/1994 | Kaufman et al. | 601/2 |
| 5,426,979 | A | * | 6/1995 | Kantorovich et al. | 73/628 |
| 5,592,943 | A | * | 1/1997 | Buhler et al. | 600/449 |
| 5,903,516 | A | * | 5/1999 | Greenleaf et al. | 367/92 |
| 6,015,383 | A | | 1/2000 | Buhler et al. | |
| 6,213,958 | B1 | * | 4/2001 | Winder | 600/586 |
| 6,322,507 | B1 | * | 11/2001 | Passi et al. | 600/437 |
| 6,585,647 | B1 | * | 7/2003 | Winder | 600/437 |

FOREIGN PATENT DOCUMENTS

| WO | WO 00/24307 | 4/2000 |
|---|---|---|
| WO | WO 00/62676 | 10/2000 |

OTHER PUBLICATIONS

Tavakoli, M.B. and Evans, J.A., "Dependence of the velocity and attenuation of ultrasound in bone on the mineral content," *Phys. Med. Biol.*, vol. 36, No. 11, 1991, pp. 1529–1537.

Laugier, P., et al., "Quantitative Ultrasound for Bone Status Assessment," *2000 IEEE Ultrasonics Symposium*, pp. 1341–1350.

* cited by examiner

*Primary Examiner*—Francis J. Jaworski
(74) *Attorney, Agent, or Firm*—Fredrikson & Byron, PA (57) ABSTRACT

Ultrasound measurement of bone quality using nonlinear analysis in combination with or alternatively using shear waves provide improved information about human bone conditions. Surface waves also provide a novel method to estimate shear wave velocity.

56 Claims, 3 Drawing Sheets

ULTRASOUND MEASUREMENT TECHNIQUES FOR BONE ANALYSIS

This application claims the benefit of provisional application No. 60/241,609 filed Oct. 19, 2000.

FIELD OF THE INVENTION

The invention relates to improved sensing and analysis of ultrasound measurement signals for use as a diagnostic tool in bone analysis.

BACKGROUND OF THE INVENTION

The field of ultrasound imaging of mammalian physiology is well known and well established. However, the methodology is dominated by certain techniques which have known limitations that are susceptible to improvement or alteration. This technology is known to be used in the imaging of various sites, such as spinal, wrist, knee, cartilaginous areas, and other musculoskeletal locations in mammals, particularly humans. The use of ultrasound for these sites generally is referred to as Quantitative Ultrasound (QUS), and is often in a competitive role with other imaging modalities.

However, there has recently been some interest in using ultrasound in a predictive role for the disease known as osteoporosis. Osteoporosis is a disease of the skeleton in which the amount of calcium present in the bones slowly decreases to the point where the bones become brittle and prone to fracture. In other words, the bone loses density. It is estimated that over 10 million people in the United States suffer from this disease, and 18 million more have low bone mass, placing them at increased risk for this disorder. Osteoporosis is no longer considered a solely age or gender-dependent, and when diagnosed early it can often be treated successfully.

In summary, osteoporosis is a major public health problem characterized by significant morbidity, mortality, and economic burden. Bone mass measurements, using ultrasound technologies, appears to be one of the best ways to make the diagnosis of osteoporosis. However, certain improvements are needed in this emerging area of medical technology to overcome reliability and availability of imaging systems.

SUMMARY OF THE INVENTION

A system and method is disclosed for diagnosing osteoporosis comprising the components and software implemented steps of transmitting a signal sequence of ultrasound waves for impingement on a bone being measured; arranging a detection transducer configuration for receiving a portion of the transmitted signal sequence of ultrasound waves after impingement on the bone being measured; and measuring the degree of acoustic nonlinearity of the bone to estimate the material conditions of the bone indicative of the onset of osteoporosis.

There is also disclosed a system and method for measuring bone strength comprising components and software implemented steps of measuring the shear wave velocity ($c_s$); estimating the Lamé coefficient shear modulus ($\mu$) of the bone by use of the formula:

$$C_s = \sqrt{\frac{\mu}{\rho}}$$

and assigning a bone strength index of measure based on the estimate of shear modulus.

There is further disclosed a system and method for diagnosing osteoporosis comprising components and software implemented steps of measuring the pressure wave velocity through a patient's bone; measuring the shear wave velocity through a patient's bone; calculating the ratio of shear wave velocity to the pressure wave velocity to determine whether the bone is degraded.

A still further disclosure includes a system for diagnosing osteoporosis comprising a transmitter configured for transmitting ultrasonic waves onto a predetermined area on the surface of a patient's skin and through the tissue to the bone so as to create a surface wave at a bone-tissue interface region that is measurable by a receiver of the ultrasonic surface wave; at least one receiver of ultrasonic waves on an area on the surface of the patient's skin a known distance from the transmitter; and analysis circuitry for measuring the surface wave velocity and translating the measured velocity into an indicator of bone health status.

DETAILED DESCRIPTION OF THE PREFERRED EMBODIMENTS

Osteoporosis is also defined as a skeletal disorder characterized by compromised bone strength predisposing to an increased risk of fracture. Bone strength reflects the integration of two main features: bone density and bone quality. Bone density is expressed as grams of mineral per area or volume and in any given individual is determined by peak bone mass and amount of bone loss. Bone quality refers to architecture, turnover, damage accumulation (e.g., microfractures) and mineralization. Osteoporosis is well established as a significant risk factor for fracture.

Osteoporosis can be further characterized as either primary or secondary. Primary osteoporosis can occur in both genders at all ages but often follows menopause in women and occurs later in life in men. In contrast, secondary osteoporosis is a result of medications, other conditions, or diseases. Osteoporosis is diagnosed when bone density has decreased to the point where fractures will happen with mild stress, its so-called fracture threshold. This is defined by the World Health Organizations as bone mass density (BMD) that is a 2.5 standard deviation (SD) or more below the average BMD for young adults. (One standard deviation below the norm in a measurement of hip bone density is equivalent to adding 14 years to a person's risk for fracture.)

Measurements of between 1 and 2.5 SD below normal are defined as osteopenia.

The consequences of osteoporosis include the financial, physical, and psychosocial, which significantly affect the individual as well as the family and community. An osteoporotic fracture is a tragic outcome of a traumatic event in the presence of compromised bone strength, and its incidence is increased by various other risk factors. Traumatic events can range from high-impact falls to normal lifting and bending. The incidence of fracture is high in individuals with osteoporosis and increases with age. Osteoporotic fractures, particularly vertebral fractures, can be associated with chronic disabling pain. Nearly one-third of patients with hip fractures are discharged to nursing homes within the year following a fracture. Notably, one in five patients is no longer living 1 year after sustaining an osteoporotic hip fracture. Hip and vertebral fractures are a problem for women in their late 70s and 80s, wrist fractures are a problem in the late 50s to early 70s, and all other fractures (e.g., pelvic and rib) are a problem throughout postmenopausal years. Indeed, the National Osteoporosis Foundation (United States) estimates that there are more than 1.5 million fractures reported each year.

By way of example, hip fracture alone has a profound impact on quality of life, as evidenced by findings that 80 percent of women older than 75 years preferred death to a bad hip fracture resulting in nursing home placement. However, little data exist on the relationship between fractures and psychological and social well-being. Other quality-of-life issues include adverse effects on physical health (impact of skeletal deformity) and financial resources. An osteoporotic fracture is associated with increased difficulty in activities of daily life, as only one-third of fracture patients regain pre-fracture level of function and one-third require nursing home placement. Fear, anxiety, and depression are frequently reported in women with established osteoporosis and such consequences are likely under-addressed when considering the overall impact of this condition. Direct financial expenditures for treatment of osteoporotic fracture are estimated at $10 to $15 billion annually. A majority of these estimated costs are due to in-patient care but do not include the costs of treatment for individuals without a history of fractures, nor do they include the indirect costs of lost wages or productivity of either the individual or the caregiver.

Currently, the most popular technique for determining bone density is dual-energy x-ray absorptiometry (DEXA), which measures bone density throughout the body within two to four minutes. The measurements are made by detecting the extent to which bones absorb photons that are generated by very low-level x-rays. Physicians use a formula based on the results of these procedures to determine if bone density has deteriorated to the fracture threshold.

Unfortunately, DEXA is not widely available and may be inappropriate for many patients. Other techniques that measure density may also result in accurate measures of overall bone loss and be less expensive and may not expose the patient to the radiation inherent to DEXA and its analogs. These are examples of the opportunities for ultrasound, subject to basic improvements in its accuracy, sensitivity, and overall predictive value.

Use of ultrasound in relation to monitoring of bone growth is also well documented. With respect to bone healing, one study reports that callus (i.e., the hard bonelike substance thrown out between and around the ends of a fractured bone) is easily visualized with ultrasound. Moreover, callus as seen on ultrasound predates its appearance on radiographs. It has also been suggested that fracture union on ultrasound precedes radiographic union. Thus, it is believed that ultrasound may provide important prognostic information concerning fracture healing as well as valuable information of regenerate bone during the process of limb lengthening.

Ultrasound has been used for many years to investigate the mechanical properties of various engineering materials. It offers the theoretic advantage of measuring material properties other than density. As noted above, this technique is termed quantitative ultrasound (QUS). This offers the advantages of small size, relatively quick and simple measurements, and no radiation. QUS measurements are generally considered as much easier to perform at skeletal sites with minimal soft tissue covering. However, to date, most QUS devices measure the peripheral skeleton, including the heel, shin, knee cap, and fingers only, due to certain limitations.

Regardless, several different QUS devices and methods have been shown to be predictive of hip fracture, independent of radiograph-based bone density measurements. QUS has enjoyed widespread use around the world and has recently been approved for clinical use in the United States. Indeed, certain changes in government reimbursement schemes may even accelerate the introduction and use of QUS technologies in order to avail lower cost high quality methodologies to a greater population. Although apparently the QUS technologies are exciting, there are still concerns and room for improvements. For example, researchers are still not certain exactly which mechanical or structural parameters of the bone are being measured with QUS. It has been speculated that QUS may be related to trabecular size, trabecular spacing, and parameters of bone mineralization such as crystal size and orientation.

In yet another analysis, it has been found that broadband ultrasound attenuation (BUA) also predicts the occurrence of fractures in older women and is a useful diagnostic test for osteoporosis. The strength of the association between BUA and fracture is similar to that observed with bone mineral density. Broad-band acoustic attenuation and speed-of-sound have also been shown to display a quantitative relationship to mineralization. Further, in another study, measurements of the attenuation and velocity of ultrasound from 0.3 to 0.8 MHz have been performed on a number of bovine cancellous bone samples. The influence of bone mineral content was isolated by measuring the acoustic properties of the samples at various stages of demineralization resulting from controlled nitric acid attack. The correlation coefficient r, between the attenuation at different frequencies and bone density was found to be in the range 0.68–0.97. Broadband ultrasonic attenuation (BUA) was also calculated and produced r values between 0.84 and 0.99. The velocity measurements indicated a correlation greater than 0.97 in all cases. Thus velocity appears to be the parameter most sensitive to changes in bone mineral density alone. Attenuation and BUA are less well correlated presumably because of a sensitivity to minor structural change. Accordingly, further advances in research are required and encouraged.

Yet another study determined that each standard deviation decrease in calcaneal broadband ultrasound attenuation was associated with a doubling of the risk for hip fractures after adjustment for age and clinic. The relationship was similar for bone mineral density of the calcaneus and femoral neck. Decreased broadband ultrasound attenuation was associated with an increased risk for hip fracture. A low broadband ultrasound attenuation value was particularly strongly correlated with intertrochanteric fractures, i.e., fractures at the proximal femur. The conclusion reached was that decreased broadband ultrasound attenuation predicts the occurrence of fracture in elderly women and that this may also provide a useful diagnostic test for osteoporosis. Thus, the need to accurately account for attenuation and sound velocity profiles of bone in patients at various sites is quite important in this fight against osteoporosis.

In summary, osteoporosis is a major public health problem characterized by significant morbidity, mortality, and economic burden. Osteoporotic fractures in older women are related, for the most part, to the women's BMD. Ultrasound does not measure bone density but rather measures two parameters called speed of sound (SOS) and broadband ultrasound attenuation (BUA) that are related to the structural properties of bone. Studies have shown that QUS measures have the ability to distinguish fracture patients from controls and to predict future fracture. The advantage for ultrasound devices is that they are small, portable, use no ionizing radiation, and may provide an attractive alternative to radiation-based densitometry. Bone mass measurement appears to be one of the best ways to make the diagnosis of osteoporosis. However, considerable improvements are needed in this emerging area of medical technology.

The methods in use for the measurement of bone density by ultrasound are generally limited to measurement of direct transmission and scatter measurements, sending sound through a bone, and measuring acoustic transmission and speed of sound, including reflection. The velocity of sound in bone can be measured using a technique analogous to that used in the field of refraction seismics, which involves investigations of the sea floor for various purposes. As applied to physiological testing, the method consists of a first transducer transmitting an ultrasonic wave from a point external of the tissue into an inner bone at a critical angle. This generates pressure, shear and/or surface waves that propagate along the interface between the bone and the soft tissue. The wave radiated from these waves is then received by a second transducer, also positioned external to the tissue. The speed of sound in the bone is calculated from the first time of arrival of the sound pulse at the receiving transducer. This method requires the velocity of sound in bone to be greater than in the surrounding soft tissue, which is true for pressure waves, but may not be fulfilled for shear waves.

Figure 1:
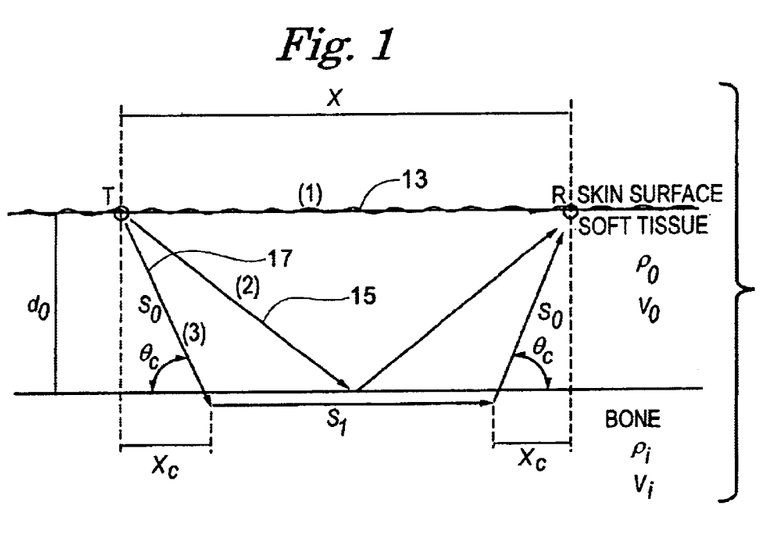
FIG. 1 is a schematic of ultrasound wave propagations in tissue and bone media.

The method is illustrated in FIG. 1, and is summarized as follows. An acoustic wave is emitted from the transmitter T into the body of the patient and received with the receiver R. T and R are placed on the skin of the patient at a distance x. The emitted wave may follow three paths from T to R:

(1) Direct wave. This wave follows a straight line parallel to the skin surface and is denoted by line 13.
(2) Reflected wave. This wave is reflected at the boundary between the soft tissue and the bone, and is denoted by line 15.
(3) Refracted wave. This wave, denoted by line 17, hits the bone at critical angle $\theta_c$, propagates along the interface between soft tissue and bone, while radiating acoustic energy back to the tissue at critical angle $\theta_c$. Some of the radiated sound is received by the receiver R. The critical angle $\theta_c$ is given by $$\theta_c = \frac{v_o}{v_1} \quad (1)$$

where $v_0$ is the speed of sound in the tissue and $v_1$ is the speed of sound in the bone.

The time of flight from T to R for these three waves are $t_1$, $t_2$ and $t_3$. The arrival time $t_3$ of the refracted wave can be found from FIG. 1 to be $$t_3 = x/v_1 + 2d_o \frac{\sqrt{v_1^2 - v_o^2}}{v_o v_1} \quad (2)$$

where x is the distance between transmitter T and receiver R and $d_0$ is the distance from the skin surface to the bone, as shown in FIG. 1.

The wave velocity $v_1$ of the bone is larger than the wave velocity $v_0$ of the soft tissue. If, in addition, the distance x between T and R exceeds a minimum value $x_{min}$, the refracted wave 17 may arrive on R before the other waves 13, 15, that is $$v_1 > v_0 \text{ and } x > x_{min} => t_3 < t_1, t_2 \quad (3)$$

Hence, the time $t_3$ can be found from the first arrival of a signal at R after transmitting from T. When the time of first arrival $t_3$ is measured, the speed of sound in the bone $v_1$ is calculated from (Eq. 2). The speed of sound in the soft tissue $v_0$ and the distances x and $d_0$ must be measured independently. This may be done from ultrasound time-of-flight measurements. This technique allows accurate measurements of sound velocity independent of geometric dimensions. This technique may be combined by one or more of the principles below to increase the accuracy of the estimates of sound velocity.

U.S. Pat. No. 5,197,475 illustrates ultrasound measurement setups using such basic principles of ultrasound pressure wave transmission and/or reflection, particularly as a function of angle. The reference provides very broad but useful description of measurement systems and techniques, and also briefly addresses the concept known as shear wave measurements. Elaborating on that latter concept, and other unknown combinations of techniques, is one of the goals of the present invention.

Shear waves do not propagate far in tissue, but will propagate in solid structures like bone. Moreover, the shear wave velocity is more sensitive to material structure than the pressure wave velocity, in that it differs more strongly between various materials. Hence, the shear wave velocity is a more sensitive parameter than pressure wave velocity for detecting the state of the measured bone.

The pressure $c_p$ and shear $c_s$ wave velocities of an elastic solid are given by the expressions $$Cp = \sqrt{\frac{\lambda + 2\mu}{\rho}} \text{ and } Cs = \sqrt{\frac{\mu}{\rho}} \quad (4)$$

where $\rho$ is the density and $\lambda$ and $\mu$ are the Lamé coefficients of the material.

Measurement of the shear wave velocity includes an estimate for the second Lamé coefficient $\mu$, which is the shear modulus of the material. Degradation of a material typically causes a reduction in its density $\rho$ and a reduction in material rigidity, that is, lower values of $\lambda$ and $\mu$. Measurements of both $c_p$ and $c_s$ in (Eq. 4) gives more information about the underlying and material properties than measurements of $c_p$ alone.

If a material undergoes a transition from an elastic solid to a looser porous structure, this causes a larger reduction in the shear modulus $\mu$ than in the bulk modulus $K=\lambda+\frac{2}{3}\mu$. Hence, independent measurements of $c_p$ and $c_s$, calculating e.g. the ratio $c_s/c_p$, will provide information about the relation between the shear and bulk moduli of the material. This gives information about whether the material is changed from an homogeneous solid into a looser porous structure.

Velocity dispersion is a characteristic property of heterogenous media, especially porous materials. If the bone undergoes a transition from homogeneous to porous, it can also change from non-dispersive to dispersive. Hence, sound velocity dispersion can be used as an indicator of altered tissue material structure. In addition, this technique can reduce the need for an accurate measurement of sound velocity, as it only requires relative measurement of phase velocity as function of frequency, and the technique does not depend on accurate measurements of geometric dimensions. In the case of a heterogenous medium, the phase velocity typically undergoes a change where the wavelength is of the same magnitude as the grain size. This transition may be used as an estimate for "grain size" in a porous material. Velocity dispersion measurements can be combined with measurement of frequency dependent attenuation, to further increase the accuracy of the estimates.

Another aspect of ultrasound imaging relates to nonlinearity. All sound propagation is nonlinear, and will generate harmonics at sufficiently high amplitudes over sufficiently long distances. Small voids or other inhomogeneities can act as nonlinear sources in solid materials, and increase the acoustic nonlinearity parameter. Hence, measurements of the degree of nonlinearity in a material can be used to estimate material conditions. Especially, it may be used to estimate whether the material is changing from a homogeneous to a more heterogenous structure.

There are several ways to measure the degree of nonlinearity. The most obvious is to transmit a sound pulse through the material and measure the harmonic distortion, i.e. the level at harmonics of the transmitted frequency. Here, the second harmonic is the most natural choice, but also higher harmonics, or combinations of harmonics can be used. Harmonic detection is summarized as Transmit frequency $f_T$
Receive one or more of the harmonics $$2f_T, 3f_T, 4f_T, \tag{5}$$

Nonlinear frequency mixing may be an even better method. Two frequencies are transmitted through the sample. This can be done either by two separate transducers, or by exciting one transducer with both frequencies. The transmitted or scattered signals from the material is picked up by another, or the same, transducer. Nonlinear mixing will cause sum- and difference frequencies in the received signals. The level at these sum and/or difference frequencies is an indicator of the condition of the material. Nonlinear frequency mixing is summarized as Transmit frequencies $f_1$ and $f_2$
Receive at sum and/or difference frequencies $$f_1+f_2, f_1-f_2 \tag{6}$$

The harmonic and nonlinear frequency mixing techniques may also be combined, i.e. receive at sum and difference frequencies of the harmonics. An example would be Transmit frequencies $f_1$ and $f_2$
Receive at sums and/or
differences around harmonics, e.g.

$$2f_1-f_2, 2f_1+f_2, 3f_1+f_{21} \tag{7}$$

The methods mentioned above may be combined in various measuring or display techniques to increase the quality of the outcomes. Further, these techniques may be combined with other measurement techniques, such as measurements of reflection, scatter, attenuation and speed of sound. They may also be combined with estimates for elastic properties, and with measurements of shape and geometrical dimensions.

In addition to the possible combinations noted above, the invention also includes a recognition of technical know how across diverse industries. For example, as is well known in the petroleum industry, porosity of materials is one of the parameters that influences acoustic velocity and attenuation. In the case of increasing porosity, a decrease in the acoustic velocities and an increase of the attenuation are expected. Moreover, it is now appreciated that compressional and shear waves can be affected differently from an increase in porosity. Past studies on acoustic P wave velocity measurements in bones were made primarily for porosity monitoring. A more efficient and suitable method for clinical use may be to measure the shear or S-wave velocity, and a combination of petroleum and medical research knowledge may be useful in that regard, as well as certain breakthrough realizations of the inventor.

Preliminary acoustic velocity measurements on bovine bones were made in order to test the possibility of measuring P-wave velocity, S-wave velocity and attenuation in bones using the equipment available in the Formation Physics Laboratory at SINTEF Petroleum Research in Trondheim, Norway. A sample description and preparation of samples in a representative bone structure comprises a compact outer layer, a cancellous bone, and inner bone marrow. Pieces of the cow bones were obtained from a butcher's shop and were preserved in a supposed best condition, but which included partially frozen matter which later caused some concern as to certain readings.

The bone to be examined is a structural bio composite of ca. 70% (by weight) inorganic calcium salts embedded in collagen fibres. Most of the inorganic phase consists of hydroxyapatite (calcium phosphate) but a large amount of carbonate, citrate and fluoride amines are also present. Long bones such as the femur or thigh bones are composed of a harder, compact composite outer layer, which improves the stiffness and strength-to-weight indices for the material, surrounding a spongy interior (cancellous bone) and the marrow. Bones exhibit viscoelastic properties and are sensitive to rate of loading.

Suitable results of the testing on the bovine samples validate the equipment and methodology suitable for advancement to tests on human bone samples. Pulse wave transmission (PWT) techniques and continuous wave techniques (CWT) were then used in order to measure compressional (Pw) and shear (Sw) wave velocities on the bovine samples TI 1–TI 5 and on the human samples TIU 1–TIU 6. The transducers used in the experiments were broadband P-wave and S-wave Panametric 500 kHz transducers for the PWT and 5 MHz for the CWT. Generally, two oppositely parallel, smooth sides were made on the samples to allow for mounting of the acoustic transducers.

The PWT equipment consisted of a WAVETEK model 278 12 MHz Programmable Synthesized Function Wave Generator, an ENI model 2100L RF 10 kHz–12 MHz amplifier, a YOKOGAWA model DL 1300A 4 Channels 100 MHz digital oscilloscope, a Physical Acoustic Corporation model 220b 40–60 dB preamplifier and filter between 100 and 1200 kHz, a computer to control the system, and a sample holder mechanism.

The continuous wave equipment consisted of a Hewlett Packard 33120A 15 MHz Function Arbitrary Waveform wave generator, a wave detector (containing) an amplifier and a modulator, a computer to control the system, and a sample holder mechanism. Measurements were made at 100, 250, 500, 750 kHz emitting frequencies, when possible. Measurements were made by CWT, both for P and S wave. The amplitude of the output signal was also recorded.

In the pulse wave techniques, the signal was sinusoidal and was generated at 230 mV and amplified by 50 dB. Corrections were made for the system delay, and the velocities were calculated using the first break criterion. For each position, 5 measurements were taken and the average value of those measurements was calculated. Acoustic velocity, amplitude and wavelength were reported. The error in the measurements was estimated to +/−2%.

Sample TI 1

P wave and S wave measurements were performed at three different positions on the bone by pulse wave technique and by using 500 kHz transducers at 100 kHz excitation frequencies. The P wave velocity was also measured at 250 kHz. It was not possible to record the output signal at 250 kHz for S-wave. Measurements were made on all three different bone structures. The measurements performed on the sample TI 1 were made in three different positions on the bone, in order to detect the velocities of the marrow, cancellous and hard zones as accurately as possible.

P wave and S wave measurements were performed by using the pulse wave technique with 500 kHz transducers at 100, 250, 500 and 750 kHz excitation frequencies. It was not possible to record the output signal at 100 kHz for S wave. Measurements were made on the cancellous zone.

TABLE 1A

TI 1

| Material | Frequency (kHz) | P wave vel (km/s) | Typical P-wave length (m) | S wave vel (km/s) | Typical S-wave length (m) | Typical A Pw Sw (v) |
|---|---|---|---|---|---|---|
| Marrow | 100 | 2.278 | 0.022 | 1.004 | 0.01 | $4 * 10^{-4}$ $5 * 10^{-4}$ |
| Cancellous zone | 100 | 2.456 | 0.024 | 1.111 | 0.011 | $1.5 * 10^{-3}$ $3 * 10^{-4}$ |
| Hard zone | 100 | 2.691 | 0.024 | | | $5 * 10^{-4}$ |

TABLE 1B

TI 1

| Material | Frequency (kHz) | P wave vel (m/s) | Typical P-wave length (m) | S wave vel (m/s) | Typical S-wave length (m) | Typical A (v) Pw |
|---|---|---|---|---|---|---|
| Marrow | 250 | 2.446 | 0.009 | | | $3 * 10^{-4}$ |
| Cancellous zone | 250 | 2.529 | 0.010 | | | $4.7 * 10^{-4}$ |
| Hard zone | 250 | 2.618 | 0.010 | | | |

Sample TI 2

TABLE 2

TI 2

| Material | Frequency (kHz) | P wave vel (km/s) | Typical P-wave length (m) | S wave vel (km/s) | Typical S-wave length (m) | Typical A (v) Pw Sw |
|---|---|---|---|---|---|---|
| Cancellous zone | 100 | 2.291 | 0.022 | | | $2.5 * 10^{-3}$ — |
| Cancellous zone | 250 | 2.395 | 0.009 | 1.552 | 0.006 | $2 * 10^{-3}$ $2 * 10^{-4}$ |
| Cancellous zone | 500 | 2.566 | 0.005 | 1.460 | 0.0029 | $1 * 10^{-3}$ $4 * 10^{-4}$ |
| Cancellous zone | 750 | 2.751 | 0.003 | 2.013 | 0.0026 | $5 * 10^{-4}$ — |

Sample TI 3

P wave and S wave measurements were performed by using the pulse wave technique with 500 kHz transducers at an excitation frequency of 100 kHz. It was not possible to record output signals at higher frequencies. The measurements were made on the cancellous zone.

TABLE 3

TI 3

| Material | Frequency (kHz) | P wave vel (km/s) | Typical P-wave length (m) | S wave vel (km/s) | Typical S-wave length (m) | Typical A (v) |
|---|---|---|---|---|---|---|
| Cancellous zone | 100 | 3.120 | 0.031 | 1.408 or (?) 1.722 | 0.015 | |

Sample TI 4

P wave and S wave velocity measurements were made by using the CWT technique on a small sample (millimeter or cutting dimension). In this case, 5 MHz transducers were used in a range of frequencies from 3 to 10 MHz. The results reported are average values of the velocities measured at all those frequencies. The measurements were made on a selected piece of the hard outer zone.

TABLE 4

TI 4

| Material | Frequency (MHz) | P wave vel (km/s) | S wave vel (km/s) |
|---|---|---|---|
| Cancellous hard zone | 3–10 | 3.83 ± (0.05) | 1.80 ± (0.04) |

Since one of the objectives of the bovine study was to validate the measuring of P and S wave acoustic velocities on bone samples and to achieve some experience with this material, the experiments were considered to be successful and indicative. Also, acoustic velocity in this bone was validated as being frequency dependent, with the velocities increasing with frequency.

Measurements on the human bone samples then occurred. The samples were already prepared at the arrival in the laboratory, and were in natural condition in plastic envelopes. Occasional grinding was necessary to enhance proper contact. A summary of the human bone sample sources is shown below in Table 5 below.

TABLE 5

| Sample | Age | Gender |
|---|---|---|
| TIU 1 | 77 | Female |
| TIU 2 | 91 | Male* |
| TIU 3 | 91 | Male* |
| TIU 4 | 95 | Female** |
| TIU 5 | 95 | Female** |
| TIU 6 | 76 | Female |

*from the same person
**from the same person

The human bone sample measurements were performed with only pulse wave techniques. Measurements were done systematically at 100, 250, 500, and 750 kHz both for P wave and S wave.

Sample TIU 1

The P wave and S wave measurements were performed by pulse wave technique and by using 500 kHz transducers at 100, 250, 500, and 750 kHz excitation frequencies. The P wave signal was clear at all frequencies even if the resolution at 750 was quite poor. The S wave signal was best defined at 250 kHz. At this frequency the two modes separated.

TABLE 6

TIU 1

| Frequency (kHz) | P wave vel (km/s) | Typical P wave length (m) | S wave vel (km/s) | Typical S wave length (m) |
|---|---|---|---|---|
| 100 | 3.18 | 0.03 | 1.45 | 0.014 |
| 250 | 3.28 | 0.01 | 1.52 | 0.006 |
| 500 | 3.40 | 0.006 | 1.57 | 0.003 |

TABLE 6-continued

TIU 1

| Frequency (kHz) | P wave vel (km/s) | Typical P wave length (m) | S wave vel (km/s) | Typical S wave length (m) |
|---|---|---|---|---|
| 750 | 3.43 | 0.004 | — | — |

Sample TIU 2

P wave and S wave measurements were performed by pulse wave technique and by using 500 kHz transducers at 100, 250, 500 and 750 kHz excitation frequencies. The P wave signal was clear at all frequencies. The S wave signal was well defined at frequencies higher than 250 kHz, and after that the sample was grounded.

TABLE 7

TIU 2

| Frequency (kHz) | P wave vel (km/s) | Typical P wave length (m) | S wave vel (km/s) | Typical S wave length (m) |
|---|---|---|---|---|
| 100 | 2.86 | 0.02 | 1.27 | 0.012 |
| 250 | 2.94 | 0.01 | 1.44 | 0.005 |
| 500 | 3.01 | 0.006 | 1.47 | 0.0029 |
| 750 | 3.16 | 0.004 | 1.53 | .002 |

Sample TIU 3

P wave and S wave measurements were performed by pulse wave technique and by using 500 kHz transducers at 100, 250, 500 and 750 kHz excitation frequencies. The P wave signal was clear at all frequencies even though the resolution at 750 kHz was poor. The S wave signal was readable only at 250 kHz and was recognized at 100 kHz.

TABLE 8

TIU 3

| Frequency (kHz) | P wave vel (km/s) | Typical P wave length (m) | S wave vel (km/s) | Typical S wave length (m) |
|---|---|---|---|---|
| 100 | 2.71 | 0.03 | 1.24 | 0.012 |
| 250 | 2.88 | 0.01 | 1.48 | 0.006 |
| 500 | 2.98 | 0.006 | — | — |
| 750 | 3.03 | 0.004 | — | — |

Sample TIU 4

P wave and S wave measurements were performed by pulse wave technique and by using 500 kHz transducers at 100, 250, 500 and 750 kHz excitation frequencies. The P wave signal was clear at all frequencies even though the resolution at 750 kHz was poor. The S wave signal was readable only at 250 kHz, but that result may be suspect.

TABLE 9

TIU 4

| Frequency (kHz) | P wave vel (km/s) | Typical P wave length (m) | S wave vel (km/s) | Typical S wave length (m) |
|---|---|---|---|---|
| 100 | 2.36 | 0.02 | — | — |
| 250 | 2.42 | 0.01 | 1.55 | 0.006 |
| 500 | 2.52 | 0.005 | — | — |
| 750 | 2.61 | 0.003 | — | — |

Sample TIU 5

P wave and S wave measurements were performed by pulse wave technique and by using 500 kHz transducers at 100, 250, 500 and 750 kHz excitation frequencies. The P wave signal was clear at all frequencies even though the resolution at 750 kHz was poor. The S wave signal was readable only at 250, 500, and 750 kHz, but the signal was poor.

TABLE 10

TIU 5

| Frequency (kHz) | P wave vel (km/s) | Typical P wave length (m) | S wave vel (km/s) | Typical S wave length (m) |
|---|---|---|---|---|
| 100 | 2.37 | 0.02 | — | — |
| 250 | 2.50 | 0.01 | 1.34 | 0.005 |
| 500 | 2.53 | 0.005 | 1.40 | 0.003 |
| 750 | 2.61 | 0.003 | 1.43 | 0.0019 |

Sample 6

P wave and S wave measurements were performed by pulse wave technique and by using 500 kHz transducers at 100, 250, 500 and 750 kHz excitation frequencies. The P wave signal was clear at all frequencies even though the resolution at 750 kHz was poor. The S wave signal was readable only at 250 and 500 kHz.

TABLE 11

TIU 6

| Frequency (kHz) | P wave vel (km/s) | Typical P wave length (m) | S wave vel (km/s) | Typical S wave length (m) |
|---|---|---|---|---|
| 100 | 2.68 | 0.03 | — | — |
| 250 | 2.74 | 0.01 | 1.18 | 0.005 |
| 500 | 2.93 | 0.006 | 1.20 | 0.002 |
| 750 | 2.96 | 0.004 | — | — |

Figure 2:
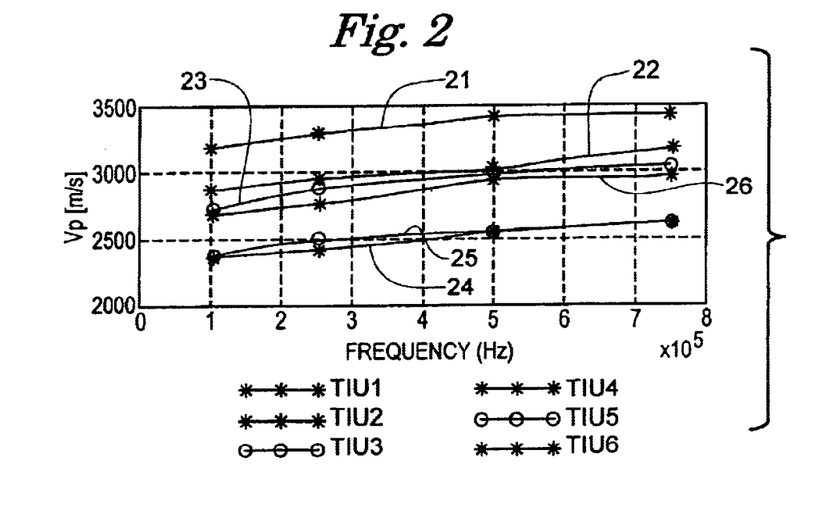
FIG. 2 is a graph of measured P waves in human samples.
Figure 3:
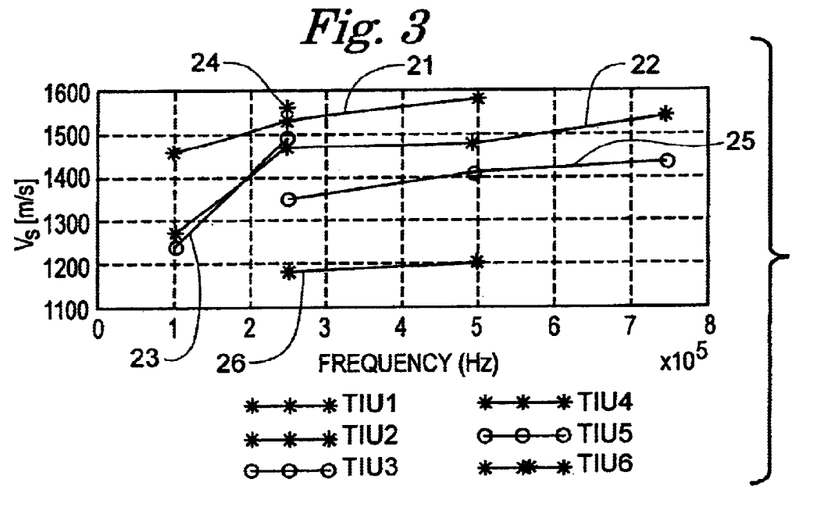
FIG. 3 is a graph of measured S waves in human samples.
Figure 4:
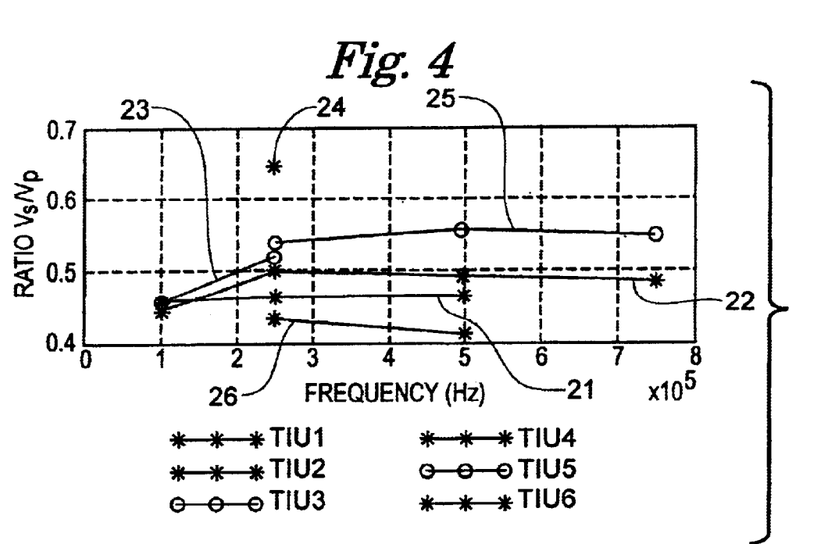
FIG. 4 is a graph of the ratio of measured S and P waves in human samples.

FIGS. 2–4 are plots of the recorded human sample P wave velocities ($V_p$), S wave velocities ($V_s$), and a ratio of the velocities ($V_s/V_p$). In these Figures, line 21 represents human sample TIU 1, line 22 represents human sample TIU 2, line 23 represents human sample TIU 3, line 24 represents human sample TIU 4, line 25 represents human sample TIU 5, and line 26 represents human sample TIU 6. Again, the main interest was in the trabecular part of the bone, as this is where the effect of osteoporosis is generally first seen.

These findings suggest that although S wave measurements were more difficult to measure than P wave measurements, the existence of a shear wave in human trabecular bone is verified. The shear wave in trabecular bone is heavily attenuated, i.e. more attenuated than the P wave. In these samples the shear wave velocity in the trabecular bone was measured at between about 1200 and 1600 m/s, depending on sample and frequency.

These results support the inventors' analysis that shear waves may be a useful measure of bone condition, including possible degradation. The shear wave velocity and/or attenuation is believed to be a more sensitive indicator of bone condition than the P wave parameters widely used in present instruments, particularly for the trabecular bone in which a marked change in shear wave velocity may indicate that normal lattice bridges and connections are no longer competent. Improved means of determining shear wave, or S wave, velocity $v_s$ and possibly attenuation $\alpha_s$, at one or more frequencies, or as a function of frequency, $v_s(f)$, $\alpha_s(f)$, are all viable techniques included herein. For example, surface waves at the bone-tissue interface provides a novel method to estimate the shear wave velocity in the bone. Surface waves at a fluid-solid interface typically have a velocity of about 0.87 and 0.95 times the shear velocity. Hence, the surface wave velocity provides a method to estimate the shear wave velocity in the bone. This is somewhat analogous to methods used to estimate the shear wave velocity in the sea floor from surface waves propagating along the water-sea floor interface.

Of particular interest are the nonlinear methods identified herein for detection of micro-cracks or micro-fractures in the human bone. These cracks may act as sources for nonlinear acoustic generation, and therefore the methods identified herein may be considered somewhat analogous to recently developed methods for detecting micro-cracks and other defects in nondestructive testing/evaluation of materials known generally as nonlinear acoustic nondestructive evaluation (NANDE) or nonlinear wave modulation spectroscopy. Measurement of acoustic nonlinearity can therefore be used as an indicator of bone condition.

Figure 5:
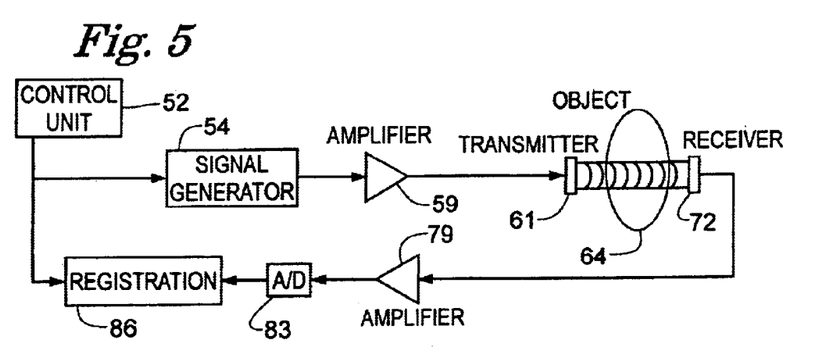
FIG. 5 is a block diagram of a pulse propagation measuring setup.
Figure 6:
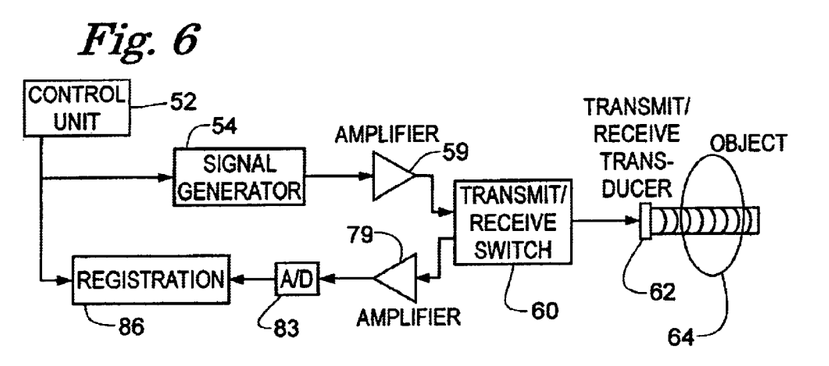
FIG. 6 is a block diagram of a backscatter or reflection measuring setup.
Figure 7:
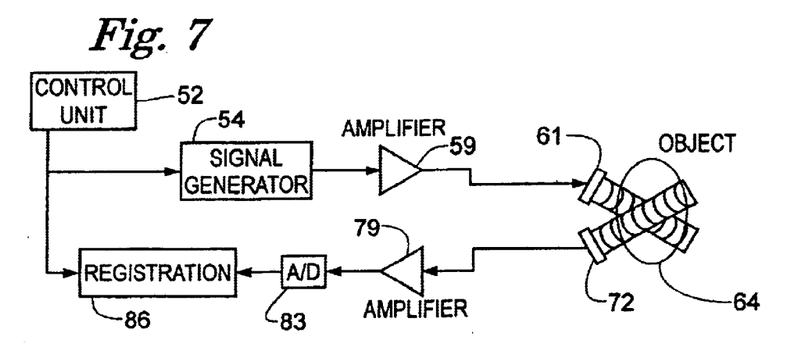
FIG. 7 is a block diagram of a reflection at an angle measuring setup.

Several of the disclosed measurement methods are considered part of this novel technique. The transmitted signal may either be a continuous wave, CW, or a pulsed wave, PW. The measurements can be accomplished as through-transmission (as shown in FIG. 5), pulse-echo backscatter (as shown in FIG. 6), or scatter at an angle (as shown in FIG. 7). In FIG. 5, there is shown representatively configured components of a control unit 52, signal generator 54, amplifier 59, transmitter 61, the object being measured 64, receiver 72, amplifier 79, analog to digital converter, and registration unit 86. The configuration of FIG. 6 includes most of the similar components but also that of transmit/receive switch 60 and transmit/receive transducer 62. In FIG. 7, the configuration is similar to that depicted in FIG. 5 but with and angled reflection setup. The detection of nonlinearity can be done by any of the following methods:

1. Two frequency mixing by transmitting two frequencies $f_1$ and $f_2$. These may then be received at the difference and/or sum frequencies $f_1-f_2$ and $f_1+f_2$;
2. Amplitude modulated signal by transmitting a signal $p=(1+A \sin 2\pi f_m t) \sin 2\pi f_0 t$ and then receiving at the modulation frequency $f_m$ and/or its harmonic, e.g., $2f_m$;
3. Transmit one high imaging frequency $f_i$ and one low pumping frequency $f_p$ and then receive at the sum and/or difference frequencies $f_i-f_p$ and $f_i+f_p$; and
4. Transmit at one frequency $f_0$ and receive at the harmonics of the transmit frequency, such as $2f_0$, $3f_0$, $4f_0$, . . . or $xf_0$.

The invention thus recognizes alternate methods and techniques to improve the quality and availability of ultrasound quantitative measurement modalities for various bone conditions. It is recognized that the various techniques may be combined with or substituted for known techniques and systems to achieve an overall improvement in this measurement capability.

What is claimed is:

1. A method of measuring bone condition using ultrasound waves, comprising the steps of:
   a) transmitting a signal sequence of ultrasound waves for impingement on a bone being measured;
   b) arranging a detection transducer configuration for receiving a portion of the transmitted signal sequence of ultrasound waves after impingement on the bone being measured; and
   c) determining the degree of acoustic nonlinearity of the bone to estimate the material conditions of the bone.

2. The method of claim 1 used for detecting bone reduction and conditions related thereto.

3. The method of claim 1 used to estimate whether the bone is changing from a homogenous to a more heterogeneous structure.

4. The method of claim 1 wherein the nonlinearity of the bone is measured with harmonic frequency detection comprising the steps of:
   a) transmitting a sound pulse through the bone; and
   b) measuring the harmonic distortion.

5. The method of claim 4 wherein the second harmonic is sensed.

6. The method of claim 4 wherein a harmonic higher than the second harmonic is sensed.

7. The method of claim 4 wherein combinations of harmonics are sensed.

8. The method of claim 1 wherein the nonlinearity of the bone is measured with nonlinear frequency mixing detection comprising the steps of:
   a) transmitting two frequencies through the bone;
   b) receiving the transmitted signals; and
   c) measuring the sum and/or difference frequencies in the received signal.

9. The method of claim 8 wherein the two frequencies transmitted are transmitted by two separate transducers.

10. The method of claim 8 wherein the two frequencies are transmitted by exciting one transducer with both frequencies.

11. The method claim 9 wherein the transmitted signals are received by one of the transducers that transmitted a frequency.

12. The method of claim 9 wherein the transmitted signals are received by a third transducer.

13. The method of claim 10 wherein the transmitted signals are received by the transducer that transmitted the frequencies.

14. The method of claim 10 wherein the transmitted signals are received by a second transducer.

15. The method of claim 1 wherein the nonlinearity of the bone is measured with a combination of harmonic detection and nonlinear frequency mixing detection.

16. The method of claim 15 further comprising the steps of:
   a) transmitting a plurality of signals at different frequencies through the bone;
   b) receiving a portion of the transmitted signals;
   c) measuring the sum and/or difference frequencies of a first transmit frequency combined with the harmonics of a second transmit frequency.

17. The method of claim 15 further comprising the steps of:
   a) transmitting two frequencies through the bone;
   b) receiving the transmitted signals;
   c) measuring the sum and/or difference frequencies of the harmonics of the transmit frequencies.

18. The method of claim 1 used in conjunction with other measurement techniques.

19. The method of claim 18 where the other measurement technique measures at least one of reflection of sound and scatter of sound.

20. The method of claim 18 where the other measurement technique measures attenuation of sound.

21. The method of claim 18 where the other measurement technique measures speed of sound.

22. The method of claim 1 used in conjunction with estimates for elastic properties.

23. The method of claim 1 used in conjunction with measurements of shape.

24. The method of claim 1 used in conjunction with measurements of geometrical dimensions.

25. A method for diagnosing osteoporosis comprising the steps of:
 a) transmitting a signal sequence of ultrasound waves for impingement on a bone being measured;
 b) arranging a detection transducer configuration for receiving a portion of the transmitted signal sequence of ultrasound waves after impingement on the bone being measured; and
 c) measuring the degree of acoustic nonlinearity of the bone to estimate the material conditions of the bone indicative of the onset of osteoporosis.

26. The method of claim 25 further comprising the step of assigning the measured bone portion a bone strength index.

27. The method of claim 26 further comprising the step of repeatedly comparing sequential time spaced measurements of the same bone structure to identify onset or susceptibility to bone disease.

28. The method of claim 25 in which the step of measuring the degree of acoustic nonlinearity of the bone comprises:
 a) transmission to achieve a two frequency mixing by transmitting two frequencies $f_1$ and $f_2$; and
 b) receipt of $f_1$ and $f_2$ at the difference and/or sum frequencies $f_1-f_2$ and $f_1+f_2$.

29. The method of claim 25 in which the step of measuring the degree of acoustic nonlinearity of the bone comprises:
 a) transmission of an amplitude modulated signal by transmitting a signal $p=(1+A \sin 2\pi f_m t)\sin 2\pi f_0 t$; and
 b) receiving the signal at a modulation frequency $f_m$ and $2f_m$.

30. The method of claim 25 in which the step of measuring the degree of acoustic nonlinearity of the bone comprises:
 a) transmission of signals comprising one high imaging frequency $f_i$ and one low pumping frequency $f_p$; and
 b) receiving the signals at sum and/or difference frequencies $f_i-f_p$ and $f_i+f_p$.

31. The method of claim 25 in which the step of measuring the degree of acoustic nonlinearity of the bone comprises:
 a) transmission of a signal comprising one transmit frequency $f_0$; and
 b) receiving the signal at a harmonic of the transmit frequency.

32. A method of measuring bone density comprising the steps of
 a) transmitting a signal having ultrasound waves for impingement on a bone;
 b) receiving at least a portion of the signal transmitted after it has impinged upon the bone;
 c) measuring the phase velocity of the received signal as a function of frequency;
 d) determining the degree of acoustic nonlinearity of the bone to estimate the material condition of the bone; and
 e) measuring the shear wave velocity of the received signal and estimating the shear modulus ($\square$) of the bone.

33. The method of claim 32 further comprising the step of measuring the frequency dependant attenuation.

34. The method of claim 32 used in conjunction with other measurement techniques.

35. The method of claim 34 where the other measurement technique measures reflection of sound.

36. The method of claim 34 where the other measurement technique measures scatter of sound.

37. The method of claim 34 where the other measurement technique measures attenuation of sound.

38. The method of claim 34 where the other measurement technique measures speed of sound.

39. The method of claim 32 used in conjunction with estimates for elastic properties.

40. The method of claim 32 used in conjunction with measurements of shape.

41. The method of claim 32 used in conjunction with measurements of geometrical dimensions.

42. A system for measuring bone density comprising:
 a) a transmitter for transmitting a signal sequence of ultrasound waves for impingement on a bone being measured;
 b) at least one receiver configured to receive at least a portion of the transmitted signal sequence of ultrasound waves after impingement on the bone being measured; and
 c) a control system configured to determine the degree of acoustic nonlinearity of the bone to estimate the material conditions of the bone.

43. The system of claim 42 wherein the acoustic nonlinearity of the bone is determined with harmonic frequency detection.

44. The system of claim 43 wherein a second harmonic is detected.

45. The system of claim 43 wherein a harmonic higher than a second harmonic is detected.

46. The system of claim 43 wherein combinations of harmonics are detected.

47. The system of claim 42 wherein the nonlinearity of the bone is determined using nonlinear frequency, the signals transmitted by the transmitter includes two frequencies and the control system measures the sum and/or the difference frequencies in the received signal.

48. The system of claim 47 wherein the transmitter comprises two transducers, each one of the transducers transmitting one of the two frequencies.

49. The system of claim 48 wherein the at least one receiver comprises one of the transducers that transmitted one of the two frequencies.

50. The system of claim 48 wherein the at least one receiver comprises a third transducer.

51. The system of claim 47 wherein the transmitter comprises a transducer that transmits the two frequencies.

52. The system of claim 51 wherein the at least one receiver comprises the transducer that transmitted the frequencies.

53. The system of claim 51 wherein the at least one receiver comprises a second transducer.

54. The system of claim 42 wherein the acoustic nonlinearity of the bone is determined using a combination of harmonic detection and nonlinear frequency mixing detection.

55. The system of claim 54 wherein the acoustic nonlinearity of the bone is determined by the transmitter transmitting a plurality of signals at different frequencies through the bone, the receiver receiving a least a portion of the transmitted signals and the control system determining the sum and/or difference frequencies of a first transmit frequency combined with the harmonics of a second transmit frequency.

56. The system of claim 55 wherein the acoustic nonlinearity of the bone is determined by the transmitter transmitting signals including two frequencies through the bone, the receiver receiving at least a portion of the transmitted signals and the control system measuring the sum and/or difference frequencies of the harmonics of the transmit frequencies.

* * * * *